United States Patent [19]

McLaren et al.

[11] Patent Number: 4,915,932

[45] Date of Patent: Apr. 10, 1990

[54] MACROAGGREGATES FOR RADIATION SYNOVECTOMY

[75] Inventors: Ashley B. McLaren, Bangor; Eric L. Hetherington; Desmond J. Maddalena, both of Kirrawee, all of Australia

[73] Assignee: Australian Nuclear Science & Technology Organisation, Australia

[21] Appl. No.: 257,384

[22] Filed: Oct. 13, 1988

[30] Foreign Application Priority Data

Oct. 14, 1987 [AU] Australia .................................. PI4880

[51] Int. Cl.$^4$ .................... A61K 43/00; A61B 6/00; C09K 11/04; C01G 57/00
[52] U.S. Cl. .................................... 424/1.1; 423/2; 600/3; 128/659; 252/625; 252/645
[58] Field of Search .................... 423/2; 252/625, 645; 424/1.1; 600/3; 128/659

[56] References Cited

U.S. PATENT DOCUMENTS 4,752,464  6/1988  Lieberman et al. .................. 424/1.1

OTHER PUBLICATIONS

Sledge, C. B. et al., "Experimental Radiation Synovectomy by DY-165 Ferric Hydroxide Macroaggregate", *Arth. & Rhemat*, vol. 20, No. 7, (9-10/1977).

*Primary Examiner*—John S. Maples
*Attorney, Agent, or Firm*—Klauber & Jackson

[57] ABSTRACT

A formulation is provided for the treatment of synovial inflammation, the formulation consisting of dysprosium-165 hydroxide macroaggregates or yttrium-90 hydroxide macroaggregates, wherein the formulation is substantially devoid of other co-precipitating agents in particular, ferric hydroxide. A method of treatment of synovial inflammation is also provided in which the method comprises adminstering an intra-articular injection of the above formulation. Preferably the above formulation is in the form of a isotonic apyrogenic injectable solution.

12 Claims, No Drawings

MACROAGGREGATES FOR RADIATION SYNOVECTOMY

FIELD OF THE INVENTION

This invention relates to the treatment of synovial inflammation of joints afflicted by arthritis, especially the knee joint, and more particularly relates to radiation synovectomy utilising preparations containing dysprosium-165 hydroxide macroaggregates or yttrium-90 hydroxide macroaggregates as an alternative to surgery.

BACKGROUND OF THE INVENTION

Rheumatoid arthritis causes significant pain and disability because more than half of the patients suffering therewith have synovial inflammation of the knee joint. Treatment is directed towards controlling the inflammation. Aspirin, non-steroidal anti-inflammatory agents and intra-articular administration of corticosteroids are treatments most commonly used.

In cases where this treatment is unsuccessful, surgical removal of the inflamed synovial membrane has been shown to give relief for 2 to 5 years. However, this method has the major disadvantage of prolonged hospitalisation, especially for older patients.

In Europe and Australia, radiation synovectomy is used as an alternative to surgery. This treatment consists of the intra-articular injection of a beta emitting radionuclide in either a colloidal or particulate form. The radiation dose destroys the inflamed tissue. Yttrium-90 and gold-198 are the most frequently used radionuclides. Very often these radionuclides have been used as colloidal suspensions, for example as a colloid of yttrium silicate.

Although radiation synovectomy has been shown to be effective for the treatment of synovitis of joints, it has not obtained widespread acceptance because of the signicant leakages that occur from the joint with these preparations. The leakage (related to particle size) when combined with the relatively long half-life of approximately 2.7 days of each results in significant integrated radiation doses to other organs, such as the lymph nodes, liver and kidneys. The lymph nodes for example can receive a dose of 9,100 rads as a result of leakage after a 185 MBq (megaBecquerals) injection of yttrium-90 silicate colloid to the knee joint.

Larger particles (macroaggregates) have been used in an effort to reduce leakage. When the radionuclide has been used in the form of the hydroxide, ferric hydroxide has always been co-precipitated, as for example with yttrium hydroxide (Y-FHMA). The ferric hydroxide has traditionally acted as a useful identifier providing a visible suspension.

Research in the USA has shown that the problem of leakage of radioactivity can also be significantly reduced by using the much shorter half-life radionuclide, dysprosium-165 (half-life 139 minutes). The preparation (Dy-FHMA) like Y-FHMA, consists of a mixture of ferric hydroxide and dysprosium hydroxide macroaggregates suspended in saline.

Surprisingly the inventors have found that a further improvement to this technique is the elimination altogether of the ferric hydroxide. Ferric hydroxide has been found to be unnecessary for the efficacy of either Dy-165 or Y-90 and in fact there is evidence to suggest that ferric ions actually induce further inflammation in arthritic joints. In addition there is the risk of a patient undergoing what is termed "iron-shock".

Whilst a suspension comprising dysprosium-165 hydroxide macroaggregates free of ferric hydroxide (Dy-HMA) is the preferred agent for patients that are less than 10 hours transport time from a reactor, a suspension of yttrium-90 hydroxide macroaggregates (Y-HMA) must still be used for patients more than 10 hours from the reactor, since the amounts of dysprosium that would need to be injected to obtain the required dose of 11 GBq, would be toxic.

SUMMARY OF THE INVENTION

According to a first aspect of the present invention there is provided a formulation for treatment of synovial inflammation, consisting of dysprosium-165 hydroxide macroaggregates or yttrium-90 hydroxide macroaggregates as the only ingredient suspended in a pharmaceutically acceptable carrier.

According to a second aspect of the present invention there is provided a formulation for treatment of synovial inflammation, consisting of dysprosium-165 hydroxide macroaggregates or yttrium-90 hydroxide macroaggregates suspended in a pharmaceutically acceptable carrier, wherein the formulation is substantially devoid of other co-precititating agents.

According to a third aspect of the present invention there is provided a formulation for treatment of synovial inflammation, consisting of dysprosium-165 hydroxide macroaggregates or yttrium-90 hydroxide macroaggregates suspended in a pharmaceutically acceptable carrier, in which there is no ferric hydroxide.

Preferably the formulation is in the form of an isotonic apyrogenic injectable solution.

According to another aspect of the present invention there is provided a method of treatment of synovial inflammation, which method comprises administering an intra-articular injection of a formulation consisting of dysprosium-165 hydroxide macroaggregates or yttrium-90 hydroxide macroaggregates as the only ingredient suspended in a pharmaceutically acceptable carrier.

According to a further aspect of the present invention there is provided a method of treatment of synovial inflammation, which method comprises administering an intra-articular injection of a formulation consisting of dysprosium-165 hydroxide macroaggregates or yttrium-90 hydroxide macroaggregates suspended in a pharmaceutically acceptable carrier, wherein the formulation is substantially devoid of other co-precipitating agents.

According to a further aspect of the present invention there is provided a method of treatment of synovia inflammation, which method comprises administering an intra-articular injection of a formulation consisting of dysprosium-165 hydroxide macroaggregates or yttrium-90 hydroxide macroaggregates suspended in a pharmaceutically acceptable carrier, in which there is no ferric hydroxide.

Preferably the carrier for the above formulation is an isotonic saline solution.

The advantages of the present formulation are that compared to Dy-FHMA and Y-FHMA:
the method of preparation is simpler and the absence of iron in the preparation avoids any problems that occur due to "iron shock" and further iron-induced inflammation of the synovial membrane.

DETAILED DESCRIPTION OF THE INVENTION

By way of example only a procedure for the preparation of dysprosium-165 hydroxide macroaggregates (DY-165 HMA) is given below.

EXAMPLE 1

Preparation of (Dy-165 HMA)

1. 35 mg of dysprosium oxide (spectrographically standardised) is neutron irradiated for 8 hours at a neutron flux of $5 \times 10^{12}$ n/s/cm$^2$.
2. The dysprosium oxide is transferred to a 10 ml Wheaton vial containing a magnetic stirring bar. The oxide is dissolved in 5.8 ml of 0.1 N HCl with stirring and heating for 5 min to boiling.
3. With rapid stirring, 1.2 ml of 0.5 N NaOH is added as quickly as possible.
4. The suspension is transferred to a 13 ml centrifuge tube, 2 ml of saline is added and the tube treated in an ultrasonic bath for 1 min.
5. The suspension is subjected to 140 g in a centrifuge for 1 minute and the supernatent discarded.
6. The dysprosium hydroxide is resuspended in 10 ml of saline and centrifuged for 1 min at 140 g. The supernatant is discarded.
7. Step 6 is repeated.
8. The dysprosium hydroxide is resuspended in 4 ml of saline and transferred to a 10 ml Wheaton serum vial.
9. After autoclaving at 132° C. for 6 min, the suspension is treated with ultrasonics for 1 min.

The final preparation contains a dysprosium concentration in the range 6–7 mg/ml and a pH of 10.5–11.0, resulting in a suspension having a dose rating of 4.5–5.5 GBq Dy-165/ml at time of callibration.

Table 1 lists the distribution of particle sizes that have been measured for 10 batches of Dy-HMA prepared by the above method. The percent of activity on particle sizes was determined by counting the activity that would pass through Nuclepore polycarbonate membrane filters. As can be seen from Table 1, Dy-HMA has the majority of particles in the 3-5 micrometer range.

Also listed in Table 1 is the distribution of particle sizes when yttrium hydroxide macroaggregates (Y-HMA) are prepared by the same method. In this case 5 mg of yttrium oxide was used and was precipitated with 2 mL of 0.1 N NaOH. With this method Y-HMA is prepared with the majority of particles in the 3-5 micrometer range (Table 1).

TABLE 1

| | Percent of Activity on Particles of Dy-HMA and Y-HMA | | | |
|---|---|---|---|---|
| | % <12 um* | % <5 um | % <3 um | % <0.45 um |
| Dy-HMA | 97–99 | 65–89 | 0.7–1.5 | <0.01 |
| Y-HMA | 98–99 | 90–98 | 1.0–2.0 | <0.01 |

*micrometer

A patient dose to the knee will require the injection of approximately 11 GBq of Dy-165. To allow for decay time due to the handling and transport from the reactor to the patient, increasing volumes of the above formulation will need to be injected as the time increases. Typical volumes for various transport times that are relevant for the Australian situation (for example ex Sydney) are listed in Table 1 below.

TABLE 2

| Volume of Injection Corrected For Transport Time | |
|---|---|
| Transport Time (hours) | Volume (ml) |
| 5 | 1 |
| 6.3 | 1.5 |
| 7 | 1.8 |
| 10 | 5 |

For an injection to the knee with a dose of 11 GBq of Dy-165.

Experiment 1: Biodistribution in Rats Injected with Dy-HMA

Biological studies in rats were performed in order to determine the leakage of radioactivity to other organs following an intra-articular injection of Dy-HMA in the knee joint. For these studies, natural dysprosium was used but spiked with a tracer level of the gamma emitting nuclide samarium-153. Approximately 10 MBq/ml of Sm-153 was co-precipitated in the formulation.

Experimental Method

Two groups of 3 healthy male rats about 300 gram were used in each experiment.

After being anaesthetised with sodium Pentabarbitone solution (30 mg/kg) each rat was given an intra-articular injection in both hind knee joints of 10 microliter. The animals were replaced in their cages unrestrained and allowed to regain consciousness. At 6 and 24 hours post injection the groups were sacrificed for tissues samples by an overdose of a sodium pentabarbitone injection.

Tissue samples were counted in a large NaI well counter.

Discussion

The results of the biodistributions are given in Table 3 (6 hours) and Table 4 (24 hours). In both Tables the average values for the 3 rats are also given.

At 6 hours, 99% of the injected dose still remains in the knee joint and the total skin value has the highest uptake of the activity that has leaked from the joint (0.83%). The majority of remaining leaked activity is then observed in the lungs ($10.1 \times 10^{-3}$%/gram) spleen ($4.98 \times 10^{-3}$%/gram) and liver ($2.48 \times 10^{-3}$%/gram).

At 24 hours, 98.5% of the injected dose remains in the knee joint with the total gastrointestinal tract (GIT) having the highest uptake of leaked activity ($6.72 \times 10^{-3}$% /gram). The majority of the remaining leaked activity is observed in the liver ($3.39 \times 10^{-3}$%/gram) spleen ($1.25 \times 10^{-3}$%/gram) $10^{-3}$%/gram) and heart ($1.12 \times 10^{-3}$%/gram).

Experiment 2: Comparison of Biodistributions in Rabbits Between Dy-HMA, Dy-FHMA and Yttrium-90 Silicate Colloid Rabbits wer chosen for these studies since the large regional lymph nodes in the legs could be obtained and counted.

The rabbits were injected in one knee joint according to the procedure described in Experiment 1. Healthy rabbits of approximately 3 Kg were used.

The results of the biodistributions at 6 and 24 hours are listed in Table 5 together with a comparison with literature results for dysprosium-165 ferric hydroxide macroaggregates (DY-FHMA- Hnatowich et al., J. Nucl., Med., 19, 303–308, 1978).

Also in Table 5 are given the biodistributions obtained when yttrium-90 silicate colloid (Amersham: Y-SC) is used. For these studies, tissue samples were dried in a hot air oven at 65 degrees C. for 1 day, 95 degrees C. for 1 day and then ashed at 250 degrees C. for two days. The ash was dissolved in 1 N HCl, diluted to 250 ml and aliquots taken, mixed with Instagel and counted in a Packard liquid scintillation counter suitable windows.

Discussion

At 6 hours, leakage to the lymph nodes with Dy-HMA is approximately the same as obtained with Dy-FHMA but less than half the leakage with Y-SC. For the liver, Dy-FHMA gives the lowest leakage with Dy-HMA and Y-SC being approximately 6 times higher. For the kidney, leakages with Dy-FHMA and Y-SC are 30 and 170 higher than with Dy-HMA At 24 hours Dy-HMA produces significantly less leakage to all the organs studied. Compared to Dy-HMA, Dy-FHMA and Y-SC Produce 2 and 6 times higher leakage to the lymph nodes; 90 and 1100 times higher to the liver; 500 and 1200 higher to the kidney and 3000 and 19 times higher to the blood, respectively.

At 72 hours leakage with Y-SC remains high in the lymph nodes and kidney.

These experiments demonstrate that Dy-HMA produces significantly less leakage compared with both Dy-FHMA and Y-SC.

Summary

Dysprosium-165 hydroxide macroaggregates (Dy-HMA) can be readily prepared as a suspension in saline. Typically, the product has a Dy concentration of 6 mg/ml and a pH in the range 10.0–11.5. The majority of particles are in the 3–5 micrometer range and there is a negligible amount of particles less than 0.45 micrometer. Dy-HMA can be autoclaved and is stable for at least twice the time it takes for the Dy-165 to decay to unusable levels.

The formulation for Dy-HMA has significant advantages over the use of both Dy-FHMA and Y-SC. The preparation is simpler and the absence of iron avoids any possibility of "iron shock" Leakages to other organs are considerably reduced.

Y-HMA can be prepared with the same formulation as Dy-HMA (e.g. paricles size range, pH) and is therefore expected to produce considerably reduced leakages similar to Dy-HMA.

TABLE 3

Biodistribution in Rats at 6 Hours Post Injection with Dy-HMA

| Organ | | | | Average |
|---|---|---|---|---|
| | % Injected Dose | | | |
| (L + R) knees | 98.1 | 98.9 | 99.7 | 99.0 |
| (L + R) legs | 0.20 | 0.01 | 0.02 | 0.04 |
| total carcass | 0.06 | 0.06 | 0.03 | 0.05 |
| skin | 1.55 | 0.90 | 0.05 | 0.83 |
| | % Injected Dose $\times 10^{-3}$/gram | | | |
| brain | 0.41 | 0.0 | 0.0 | 0.14 |
| total GIT | 2.80 | 1.84 | 0.63 | 1.76 |
| urine + bladder | 0.47 | 0.38 | 0.25 | 0.37 |
| blood | 0.03 | 1.07 | 0.04 | 0.38 |
| heart | 0.48 | 3.00 | 0.0 | 1.16 |
| lung | 0.03 | 2.92 | 27.4 | 10.1 |
| kidney | 0.18 | 2.91 | 0.83 | 1.31 |
| spleen | 0.07 | 5.52 | 9.36 | 4.98 |
| liver | 0.56 | 1.14 | 5.76 | 2.48 |

TABLE 4

Biodistribution in Rats at 24 Hours Post Injection with Dy-HMA

| Organ | | | | Average |
|---|---|---|---|---|
| | % Injected Dose | | | |
| (L + R) knees | 98.0 | 98.5 | 98.8 | 98.5 |
| (L + R) legs | 0.51 | 0.08 | 0.06 | 0.10 |
| total carcass | 1.23 | 1.25 | 1.04 | 1.17 |
| skin | 0.01 | 0.01 | 0.0 | 0.03 |
| | % Injected Dose $\times 10^{-3}$/gram | | | |
| brain | 0.02 | 0.58 | 0.98 | 0.53 |
| total GIT | 12.08 | 3.98 | 4.17 | 6.72 |
| urine + bladder | 0.69 | 1.67 | 0.37 | 0.91 |
| blood | 0.03 | 0.04 | 1.18 | 0.42 |
| heart | 1.03 | 0.49 | 1.85 | 1.12 |
| lung | 0.53 | 0.10 | 0.02 | 0.22 |
| kidney | 0.69 | 0.62 | 1.35 | 0.89 |
| spleen | 0.07 | 0.92 | 2.75 | 1.25 |
| liver | 4.08 | 4.49 | 1.61 | 3.39 |

TABLE 5

Comparison of Biodistributions in Rabbits Between Dy-HMA, Dy-FHMA and Yttrium Silicate Colloid (Y—SC)

| | Time | Rab. | Lymph | Liver | Kidney | Blood |
|---|---|---|---|---|---|---|
| Dy-HMA | 6 | 3 | 0.83 | 4.3 | 0.9 | 0.024 |
| | | | (0.0–1.5) | (0.0–12.9) | (0.0–2.2) | (0.0–0.63) |
| Dy-FHMA | 5 | 7 | 1.0 | 0.7 | 27 | 17 |
| | | | (0.0–3.3) | (0.2–1.3) | (5–83) | (4–49) |
| Y—SC | 6 | 3 | 1.9 | 5.4 | 160 | 0.23 |
| | | | (1.0–1.5) | (3.5–7.0) | (123–209) | (0.0–0.44) |
| Dy-HMA | 24 | 3 | 1.5 | 0.04 | 0.27 | 0.01 |
| | | | (0.0–3.5) | (0.01–0.07) | (0.0–0.50) | (0.0–0.015) |
| Dy-FHMA | 24 | 5 | 3.0 | 3.7 | 140 | 34 |
| | | | (0.7–12) | (1.7–6.3) | (21–326) | (4–77) |
| Y—SC | 24 | 3 | 8.9 | 44 | 332 | 0.19 |
| | | | (6–10) | (5.117) | (256–487) | (0.02–0.45) |
| Y—SC | 72 | 3 | 11.3 | 2.7 | 70 | 0.31 |
| | | | (0–21) | (1.6–3.3) | (45–90) | (0.0–0.93) |

Time: hours
Rab.: number of rabbits
Lymph: % injected dose $\times 10^{-3}$
Liver: % injected dose $\times 10^{-3}$/gram
Kidney: % injected dose $\times 10^{-3}$ for one kidney
Blood: % injected dose $\times 10^{-3}$/ml
DY-FHMA: Literature results, Hnatowich, D. J., Kramer, R. I., Sledge, C. B., Noble J., and Shortkroff, S. - Journal Nuclear Medicine, 19(3), 303–308, 1978.

We claim:

1. A formulation for treatment of synovial inflammation consisting of an active ingredient selected from the group consisting of dysprosium-165 hydroxide macroaggregates and yttrium-90 hydroxide macroaggregates, as the only ingredient suspended in a pharmaceutically acceptable carrier.

2. A formulation for treatment of synovial inflammation, consisting of an active ingredient selected from the group comprising dysprosium-165 hydroxide macroaggregates and yttrium-90 hydroxide macroaggregates, suspended in a pharmaceutically acceptable carrier, wherein the formulation is substantially devoid of other co-precititating agents.

3. A formulation for treatment of synovial inflammation, consisting of an active ingredient selected from the group comprising dysprosium-165 hydroxide macroaggregates and yttrium-90 hydroxide macroaggregates, suspended in a pharmaceutically acceptable carrier, in which there is no ferric hydroxide.

4. A formulation according to claim 1 in which the formulation is in the form of an isotonic apyrogenic injectable solution.

5. A formulation according to claim 2 in which the formulation is in the form of an isotonic apyrogenic injectable solution.

6. A formulation according to claim 3 in which the formulation is in the form of an isotonic apyrogenic injectable solution.

7. A method of treatment of synovial inflammation in human subjects, which method comprises administering to said subject an intra-articular injection of an effective amount formulation consisting of an active ingredient selected from the group consisting of dysprosium-165 hydroxide macroaggregates and yttrium-90 hydroxide macroaggregates, as the only ingredient suspended in a pharmaceutically acceptable carrier.

8. A method of treatment of synovial inflammation in human subjects, which method comprises administering to said subject an intra-articular injection of an effective amount a formulation consisting of an active ingredient selected from the group consisting of dysprosium-165 hydroxide macroaggregates and yttrium-90 hydroxide macroaggregates, suspended in a pharmaceutically acceptable carrier, wherein the formulation is substantially devoid of other co-precipitating agents.

9. A method of treatment of synovial inflammation in human subjects, which method comprises administering to said subject an intra-articular injection of an effective amount formulation consisting of an active ingredient selected from the group consisting of dysprosium-165 hydroxide macroaggregates and yttrium-90 hydroxide macroaggregates, suspended in a pharmaceutically acceptable carrier, in which there is no ferric hydroxide.

10. A method according to claim 7 in which the carrier for the above formulation is an isotonic saline solution.

11. A method according to claim 8 in which the carrier for the above formulation is an isotonic saline solution.

12. A method according to claim 9 in which the carrier for the above formulation is an isotonic saline solution.

* * * * *